United States Patent
Devlin, Sr. et al.

(10) Patent No.: US 6,723,288 B2
(45) Date of Patent: Apr. 20, 2004

(54) METHOD OF PROVIDING ASSAY PROCESSING IN A MULTI-ANALYZER SYSTEM

(75) Inventors: William Jackson Devlin, Sr., Lincoln University, PA (US); David Russell Thompson, Kennett Square, PA (US)

(73) Assignee: Dade Behring Inc., Deerfield, IL (US)

( * ) Notice: Subject to any disclaimer, the term of this patent is extended or adjusted under 35 U.S.C. 154(b) by 103 days.

(21) Appl. No.: 10/373,297

(22) Filed: Feb. 24, 2003

(65) Prior Publication Data

US 2003/0202905 A1 Oct. 30, 2003

Related U.S. Application Data

(60) Provisional application No. 60/376,256, filed on Apr. 29, 2002.

(51) Int. Cl.$^7$ .............................................. G01N 35/02
(52) U.S. Cl. ............................ 422/65; 422/63; 422/64; 422/67; 436/43; 436/47; 436/48; 436/50; 700/266
(58) Field of Search .................. 422/63–67; 436/43, 436/47, 48, 50; 700/266

(56) References Cited

U.S. PATENT DOCUMENTS

| | | | | |
|---|---|---|---|---|
| 5,087,423 A | * | 2/1992 | Ishibashi | |
| 5,209,903 A | * | 5/1993 | Kanamori et al. | 422/65 |
| 5,380,488 A | * | 1/1995 | Wakatake | |
| 5,902,549 A | * | 5/1999 | Mimura et al. | 422/65 |
| 5,966,309 A | * | 10/1999 | O'Bryan et al. | 700/225 |
| 5,972,295 A | * | 10/1999 | Hanawa et al. | 422/65 |
| 6,019,945 A | * | 2/2000 | Ohishi et al. | 422/65 |
| 6,022,746 A | * | 2/2000 | Fritchie et al. | 436/50 |
| 6,060,022 A | * | 5/2000 | Pang et al. | 422/65 |
| 6,117,392 A | * | 9/2000 | Hanawa et al. | 422/65 |
| 6,141,602 A | * | 10/2000 | Igarashi et al. | 700/226 |
| 6,261,521 B1 | * | 7/2001 | Mimura et al. | 422/67 |
| 6,290,907 B1 | * | 9/2001 | Takahashi et al. | 422/65 |

* cited by examiner

*Primary Examiner*—Jill Warden
*Assistant Examiner*—Kathryn Bex
(74) *Attorney, Agent, or Firm*—Leland K. Jordan

(57) ABSTRACT

A multi-analyzer system where at least two automatic clinical analyzers are linked together by a bi-directional sample rack shuttle, both analyzers initially capable of performing a slightly different menu of assays. The bi-directional incoming and outgoing sample rack transport system of a first one of the two analyzers is automatically converted into a one-way incoming sample rack transport system adapted and the incoming sample tube transport system of a second of the two analyzers is automatically converted into a one-way outgoing transport system adapted to dispose of all sample racks having sample tubes with samples finally tested by either analyzer. In the event that one of the two analyzers experiences an operating failure, the analyzer system may automatically revert to a single analyzer system employing only the operational analyzer.

7 Claims, 8 Drawing Sheets

METHOD OF PROVIDING ASSAY PROCESSING IN A MULTI-ANALYZER SYSTEM

This application claims priority of U.S. Ser. No. 60/376,256, filed Apr. 29, 2002.

FIELD OF THE INVENTION

The present invention relates to a method and apparatus for automatically processing a patient's biological fluids such as urine, blood serum, plasma, cerebrospinal fluid and the like. In particular, the present invention provides a method to perform assays in an analyzing system having at least two analyzers each adapted to perform a number of clinical assays using various assay technologies.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction vessels or tubes, incubated, and analyzed to aid in treatment of the patient. In typical clinical chemical analyses, one or two assay reagents are added at separate times to a liquid sample having a known concentration, the sample-reagent combination is mixed and incubated. Interrogating measurements, turbidimetric or fluorometric or absorption readings or the like are made to ascertain endpoint or rate values from which an amount of analyte may be determined using well-known calibration techniques.

Although various known clinical analyzers for chemical, immunochemical and biological testing of samples are available, analytical clinical technology is constantly challenged by increasing needs for improved sample analysis. Due to increasing demands on clinical laboratories regarding assay throughput, there continues to be a need for improvements in the overall performance of automated clinical analyzers. In particular, sample analysis continuously needs to be made more efficient in terms of reduced analyzer downtime, caused by a number of factors, which has aggravated by recent efforts to increase analyzer throughput, in particular, by linking together a number of analyzers and conveying samples between the analyzers.

An important contributor to maintaining a high throughput of automatic analyzers is the ability to quickly process a plurality of samples through a variety of different assay process and signal measurement steps. One method to achieve this feature is to serially link together analytical modules of different types, each adapted to perform a certain catalog of assays. Another is to link together two or more analyzers of the same type and to allocate incoming samples to whichever analyzer has the smallest backlog of samples to process. Alternately, incoming samples may be allocated between analyzers according to the number and availability of assay resources (reaction vessels, reagents, etc) required by the assay and duplicated on more than one analyzer. What has been overlooked, however, in the design of such prior art systems, is that throughput and/or reliability of multi-analyzer systems may be adversely affected in the event of performance failure in operational portions of either of the analyzers, analytical modules, sample entry and exit areas and/or in the conveyor means that link together two or more of the analyzers.

U.S. Pat. No. 6,261,521 discloses a sample analysis system having a plurality of analysis units placed along a main conveyor line prior to its analysis operation. The system setup includes setup of analysis units in combination with different types of reagent supply units, setup of analysis routes as to whether it is a stationary type or an automatic type, and setup of analysis items for each analysis unit as to which analysis item should be assigned to which analysis unit having which reagent supply type.

U.S. Pat. No. 6,117,392 discloses an automatic analyzing apparatus having a rack supply unit capable of containing sample racks, an analyzing unit for testing a sample sampled from a sample container contained in the sample rack, a transfer line for transferring a sample rack supplied from the rack supply unit to a position corresponding to the analyzing unit and transferring the sample rack after being sampled to an exit of the transfer line, a standby unit for keeping sample racks having a probability of being reexamined standing-by, a returning line for returning the sample rack after being sampled to an entrance side of the transfer line, and a rack collecting unit for containing sample racks not required to be reexamined.

U.S. Pat. No. 6,022,746 discloses a method for operating a multi-analyzer system by generating a list of tests to be performed by the system within a given reaction vessel. The list of tests is sorted according to the number of reaction vessels used in performing each test to be performed by the system in a given time period. A duplication percentage for the tests is determined and is compared with the sorted list of tests. Resources associated with the tests are duplicated across at least two analyzers based on the comparison of the duplication percentage with the sorted list of tests in a matter that at least one of the tests is performed by at least two of the analyzers.

U.S. Pat. No. 6,019,945 discloses a transfer mechanism for transferring a sample container holder between a conveyor line and a sampling area formed in each of several analyzers, the transfer mechanism being connectable to each one of the plurality of analyzers. At least two analyzers units are different from one other in either the types of reagent supply means, the number of analysis items that can be analyzed, the number of tests that can be processed in a unit time, or the species of samples to be processed. The at least two analysis units described above have the same attachment mechanism or the same shape thereof with respect to the conveyor line.

U.S. Pat. No. 5,972,295 discloses an automatic analyzers comprising a rack supply unit capable of containing sample racks, an analyzing unit for testing an instructed analysis item to a sample sampled from a sample container contained in the sample rack, a transfer line for transferring a sample rack supplied from the rack supply unit to a position corresponding to the analyzing unit and transferring the sample rack after being sampled to an exit of the transfer line, a standby unit for keeping sample racks having a probability of being reexamined stand-by, a returning line for returning the sample rack after being sampled to an entrance side of the transfer line, and a rack collecting unit for containing sample racks not required to be reexamined.

U.S. Pat. No. 5,966,309 discloses an automated apparatus for subjecting samples to one or more selected test procedures at one or more test stations comprising a conveyor line for transporting samples contained in uniquely labeled containers, said line having at least two lanes for routing said containers to one or more selectable test stations, at least one of said lanes being a transport lane and at least one of said lanes being a queue line, and having a container interface device for transferring containers to said testing device from the queue lane and back again onto said queue lane.

U.S. Pat. No. 5,902,549 discloses a plurality of analyzer units for serum, a plurality of analyzer units for blood plasma, and a plurality of analyzer units for urine are arranged along a main transfer line for transferring a sample rack from a rack providing portion to a rack storage portion. A reagent bottle for inspecting liver function is contained in each reagent delivery mechanism of two analyzer units among the plurality of analyzer units for serum. When the reagent for inspecting liver function in one of the two analyzer units is to be short, analysis for the liver function analysis item in the samples can be continued by transferring a sample rack from the rack providing portion to the other analyzer unit.

U.S. Pat. No. 5,380,488 discloses a container feeding system which includes a feed stocker for stocking racks holding containers, one or more sampling feeders connected to the downstream side of the feed stocker, and one or more analyzers for withdrawing samples from containers which are moved to sampling positions in an interlocked relation to the sampling feeder or feeders. One or more coupling feeders are connected to the respective downstream sides of the sampling feeder or feeders, and a treated container stocker is connected to the most downstream side of the coupling feeder or feeders. The individual components are provided as respective units. The number of sampling feeders and coupling feeders connected thereto can be increased or reduced, and in correspondence therewith so can the number of analyzers disposed along a rack feeding line. The rack feeding path can thus be readily increased and reduced, as desired, to meet the scale of the delivery side. Likewise, the control mechanism for controlling the feeding of containers with selective priority is also greatly simplified.

U.S. Pat. No. 5,087,423 discloses a plurality of analyzing modules, a plurality of analyzing routes and at least one bypass route bypassing at least one analyzing module are arranged. Each analyzing module is capable of analyzing samples with respect to one or more items, and samples successively supplied from the introduction sides of the modules are selectively delivered into each module in accordance with the possible analyzing items of each module and the analyzing items of the samples to be analyzed. The sample cup can pass the module via a bypass or can be returned to the introduction side of the module via a bypass, in accordance with the items to be analyzed, the effective distribution of the sample cups can be performed.

From this discussion of the art state in automated clinical analyzers, it may be seen that while progress has been made toward increasing processing efficiency, there remains an unmet need for a method for operating a multi-analyzer system in a way that enhances the reliability of multi-analyzer systems. In particular, little progress has been made toward increasing the reliability of operation of a multi-analyzer system by providing back-up operational capability in the event of performance failure in various operating portions of any of the analyzers and/or in the conveying means that link together the analyzers.

SUMMARY OF THE INVENTION

The principal object of the invention is to provide a method for using a clinical analyzer system where at least two automatic clinical analyzers are linked together, that is a multi-analyzer system having two or more analyzers connected together in a manner that ensures system throughput and/or reliability in the event of machine or performance failure in operating portions of either of the analyzers and/or in the connecting means that link together the analyzers.

Each analyzer includes a circular rotatable assay reaction carousel for holding reaction vessels and providing stepwise movements in a circular direction, the stepwise movements being separated by stationary dwell times, during which dwell times an assay device may operate on an assay mixture contained within a reaction vessel. A multi-analyzer system like those on which the present invention may be performed typically has a plurality of conventional assay operation stations at which are positioned individual assay devices, such as sensors, reagent add stations, mixing stations, separation stations, and the like.

In an exemplary embodiment of the present invention, a key feature is that at least two automatic clinical analyzers are linked together by a bi-directional shuttle, the bi-directional shuttle adapted to move only a single sample rack or only a similar device between said analyzers. The two analyzers are essentially machine-wise identical to one another except that the menu of assays capable of being performed on the individual analyzers may be optionally and selectively different; i. e., both analyzers are equipped with physically identical sample handling, reagent storage and sample processing and assaying devices, etc. However, both analyzers may be equipped with a slightly different inventory of reagents stored on-board each so that the analyzers are initially capable of performing a slightly different menu of assays. In a stand-alone mode, each analyzer has an independently operable bi-directional incoming and outgoing automated sample rack transport system, so that samples to be tested may be placed onto an analyzer, automatically subjected to the requested assay protocols, and returned to an inventory of samples finally tested. However, when the machines are linked together by a bi-directional shuttle, the bi-directional incoming and outgoing sample rack transport system of a first one of the two analyzers is automatically converted into a one-way incoming sample rack transport system adapted to receive all sample racks carrying sample tubes to be analyzer by either analyzer. In a similar manner, the incoming sample tube transport system of a second of the two analyzers is automatically converted into a one-way outgoing transport system adapted to dispose of all sample racks having sample tubes with samples finally tested by either analyzer. Because the bi-directional shuttle is adapted to move only a single sample rack or similar device between analyzers, in the event that one of the two analyzers experiences an operating failure or in the event that the bi-directional shuttle experiences an operating failure, the analyzer system may automatically revert to a single analyzer system employing only the operational analyzer and samples may be supplied only to and analyzed only by the operational analyzer.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
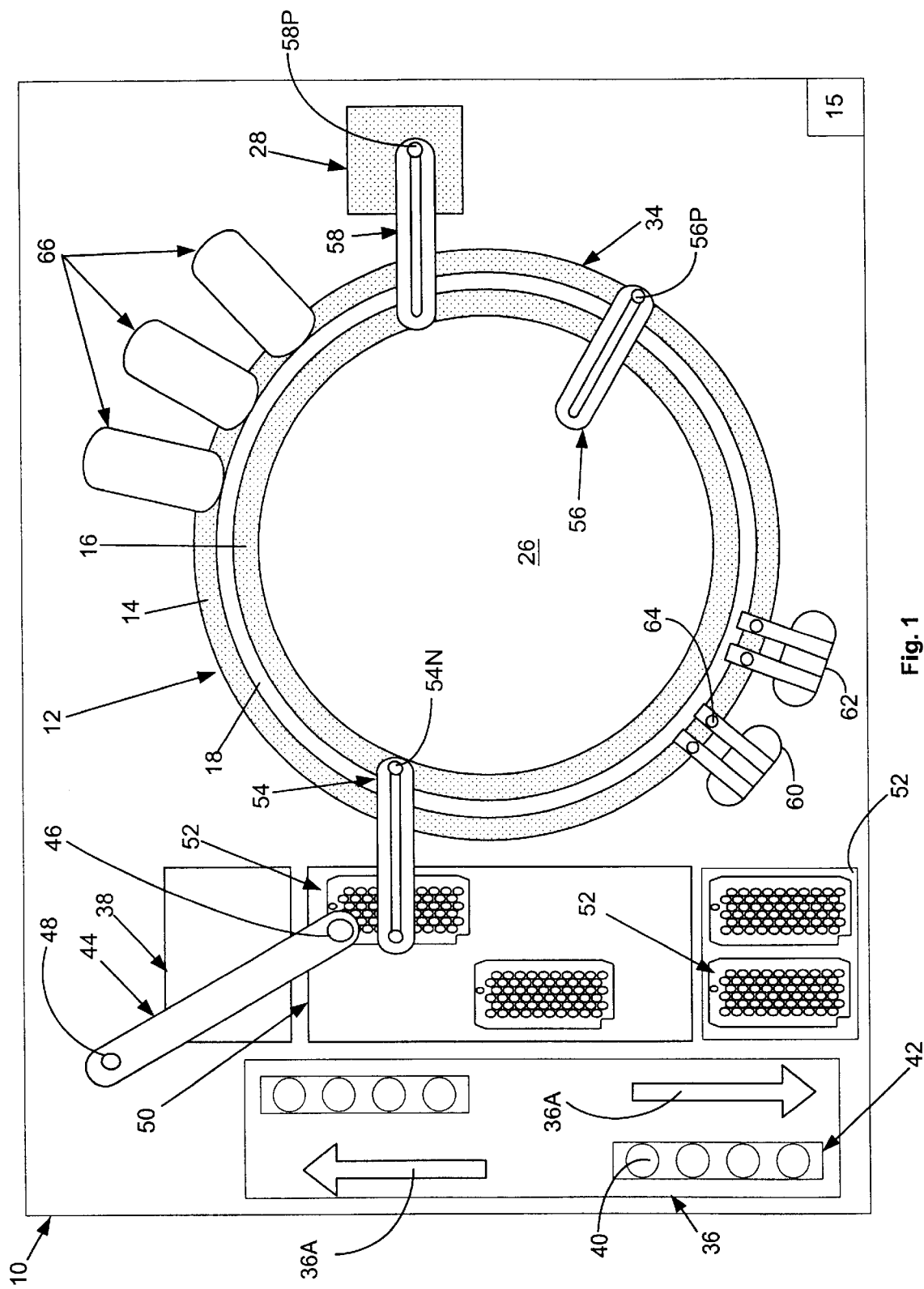
FIG. 1 is a schematic plan view of a single conventional automated clinical analyzer like those known in the art.
Figure 2:
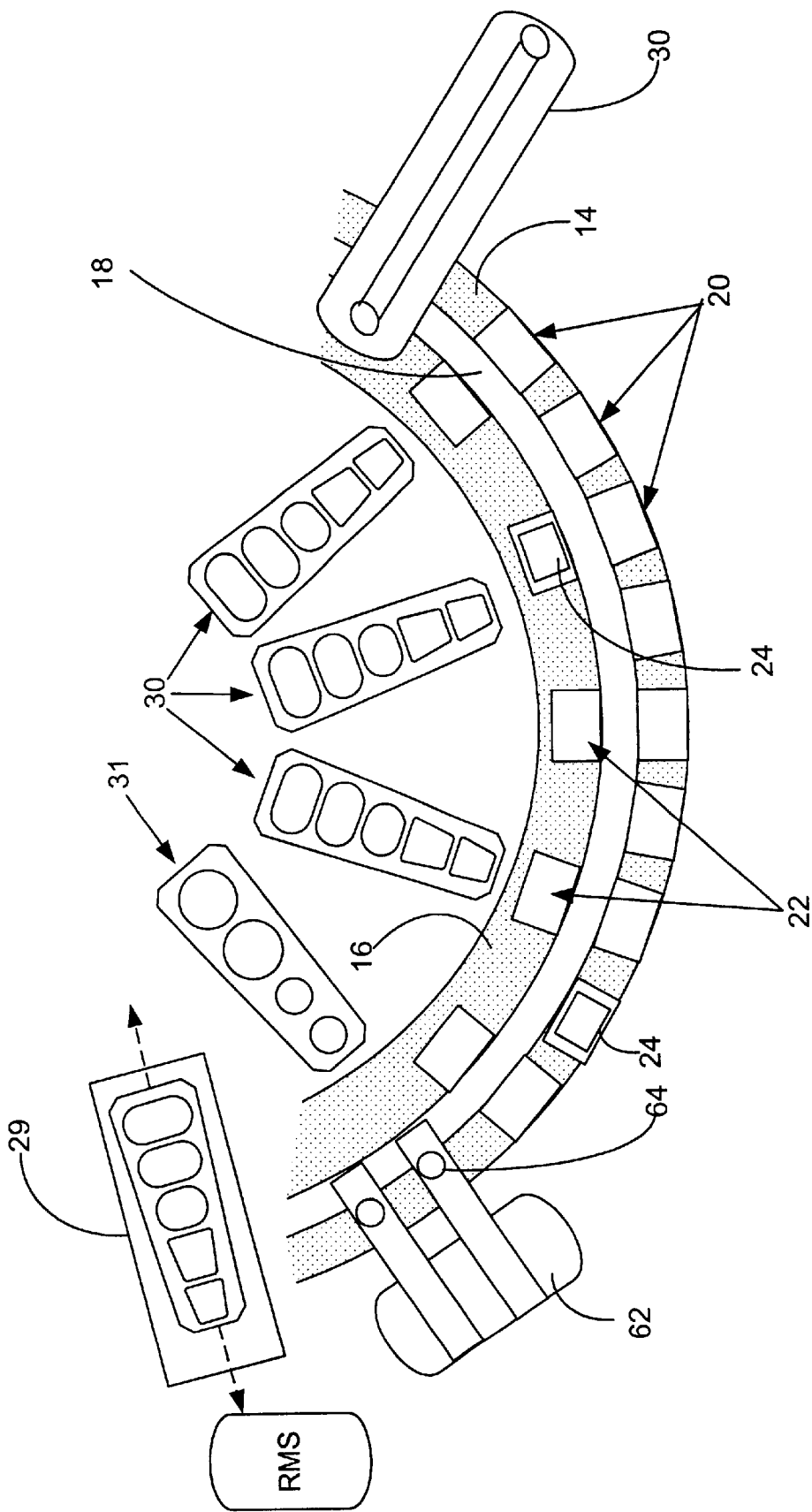
FIG. 2 is an enlarged partial schematic plan view of the automated analyzer of FIG. 1.

FIG. 1, taken with FIG. 2, shows schematically the elements of a single convention automatic chemical analyzer 10 convenient for practicing the present invention and comprising a reaction carousel 12 supporting a outer cuvette circle 14 of cuvette ports 20 and an inner cuvette circle 16 of cuvette ports 22, the outer cuvette circle 14 and inner cuvette circle 16 being separated by a open groove 18. Cuvette ports 20 and 22 are adapted to receive a plurality of reaction cuvettes 24 typically formed as small, flat walled, U-shaped containers with an open central reaction portion closed at the bottom and with an opening at the top of the cuvettes 24 to allow the addition of reagent and sample liquids. Reaction carousel 12 is rotatable using stepwise movements in a constant direction at a constant velocity, the stepwise movements being separated by a constant dwell time during which dwell time, carousel 12 is maintained stationary and an assay device located proximate carousel 12 may operate on an assay mixture contained within a cuvette 24.

Two temperature-controlled reagent storage areas 26 and 28 each store a plurality of reagent cartridges 30, cartridges 30, for example being a multi-compartmented reagent container like those described in U.S. Pat. No. : 4,720,374, or co-pending application Ser. No.: 09/949,132 assigned to the assignee of the present invention, and sold under the tradename FLEX™ cartridge by Dade Behring Inc, Deerfield, Ill., and containing reagents as necessary to perform a given assay. A selectively-opened lid (not shown) covers each of reagent storage areas 26 and 28 to allow access to cartridges 30; for simplicity, only three reagent cartridges 30 are schematically illustrated in FIG. 2 as disposed beneath a cut out portion of reagent storage area 26 however similar reagent cartridges 30 are disposed within reagent storage area 28. Shuttle means (not shown) move individual cartridges 30 to access ports for reagent probes 56P and 58P discussed later. Storage area 28 may be conveniently located external to the circumference of outer cuvette circle 14 and reagent storage area 26 may be conveniently located internal to the circumference of inner cuvette circle 16. A reagent management system transport 29 is provided to move reagent cartridges 30 and special" reagent cartridges 31" described later into either storage area 26 and/or to storage area 28 from an external reagent management system RMS of reagent cartridges 30.

A clinical analyzer 10 like those on which the present invention may be performed has a plurality of conventional assay operation devices 34 disposed proximate carousel 12 and at which are positioned individual computer controlled electro-mechanical devices, such as sensors, reagent add stations, mixing stations, and the like, as required to perform the myriad of actions required in well known clinical assays. Such devices and their operation are well known in the art and need not be described herein. See, for example, U.S. Pat. Nos. 5,876,668, 5,575,976 and 5,482,861 and the references cited therein.

An indexing drive for the reaction carousel moves the reaction vessels in the constant direction a predetermined numbers of incremental steps. The length of the circumference of cuvette circles 14 and 16, the separation distance between cuvette ports 20 and 22, the number of cuvette ports 20 and 22, and the number of increments per indexing are selected so that any given cuvette ports 20 and 22 returns to its original starting position after a fixed number of incremental steps. Thus, all cuvette ports 20 and 22 on the reaction carousel 12 return to their original location in a full operational cycle time which is determined by the fixed number of incremental steps multiplied by the sum of dwell time at each assay device and the time required for a stepwise movement.

Figure 3A:
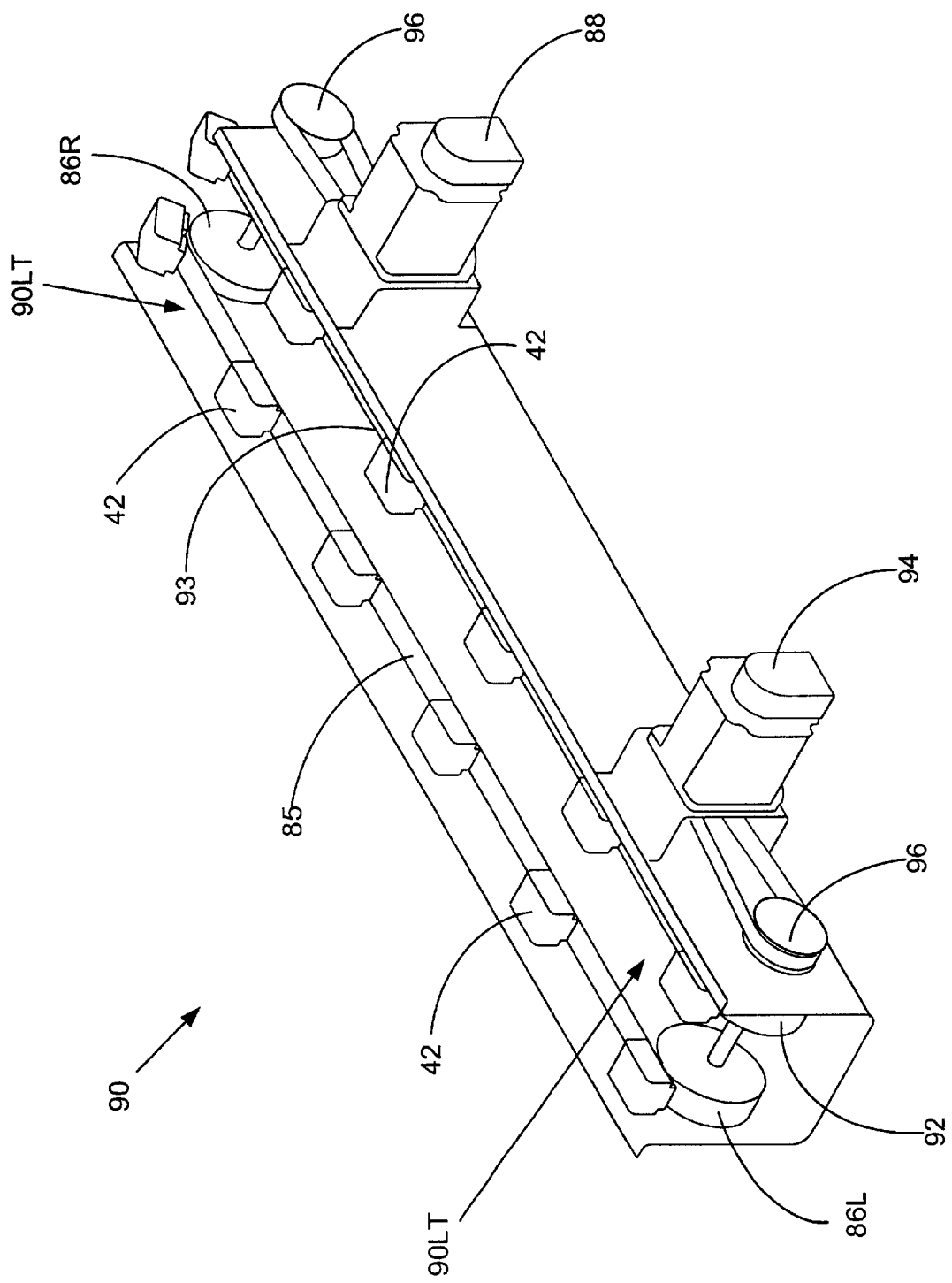
FIGS. 3A and 3B are perspective view of a sample rack transport system useful in practicing the present.

Incoming sample specimens to be tested are contained in sample tubes 40 mounted in sample tube racks 42 and transported into the arc of sampling arm 44, for example, by a bi-directional incoming and outgoing automated sample rack transport system 36, so that samples to be tested may be placed onto an analyzer, automatically subjected to the requested assay protocols, and returned to an inventory of samples finally tested, as indicated by open arrows 36A, and as described in co-pending application Ser. No.: 09/992,917 assigned to the assignee of the present invention. This system is described further here for illustration even though this method of transporting sample 30 tube racks 42 of a magnetic type is not definitive nor limiting as several other mechanisms capable of bi-directionally transporting incoming and outgoing sample racks are well known in the art. A magnetic drive system 90 useful in analyzer 10 for carrying out the present invention is seen in the perspective drawings of FIG. 3A to comprise at least one bi-directional linear drive transport mechanism 90LT depicted, for example, as a first belt 85 endlessly circulating around a first pair of pulleys 86, one of the first pulleys 86 being coupled to a first bi-directional motor 88, the first belt 85 and first pulleys 86 being mounted beneath and in close proximity to the operating surface of analyzer 10 which defines input and output lanes. FIG. 3A illustrates two such bi-directional linear drive transport mechanisms 90LT, however, in a first embodiment of the present invention described later in which a single incoming sample tube transport system 70 is employed, only a single bi-directional linear drive transport mechanism 90LT is required to practice the present invention. It should be understood that any of several mechanisms are capable of providing the bi-directional linear drive transport mechanism 90LT used within the present invention, for instance a bi-directional motor coupled to a linear drive screw, or a pneumatic operated plunger, both supporting the magnetic housings and having a magnet therein.

Figure 3B:
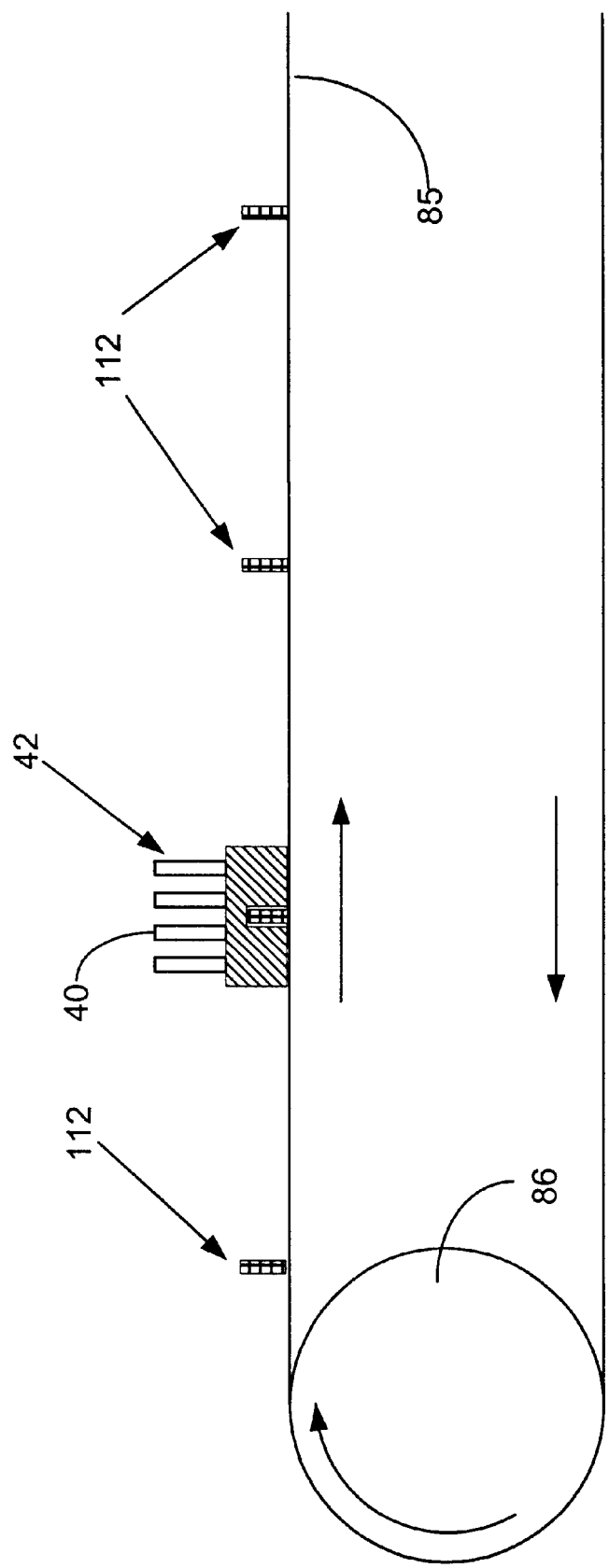

First belt 85 is driven by motor 88 in an incoming direction, for example along the direction of arrow 36A, and is located beneath the operating surface of analyzer 10. In a similar manner, magnetic drive system 90 comprises a second belt 93 endlessly circulating around a second pair of pulleys 92, one of the second pulleys 92 (only one such pulley 92 is visible) being coupled to a second bi-directional motor 94, the second belt 93 and second pulleys 92 being mounted beneath and in close proximity to the output lane 74 portion of the operating surface of analyzer 10. Second belt 93 is driven by second motor 94 in a second direction opposite to the first direction. Motors 88 and 94 are typically stepper motors independently controlled by computer 15 and have drive gears 96 coupled to pulleys 86 and 92 which are preferably formed as pulley gears interlaced with gear teeth formed on belts 85 and 93. The magnetic drive system 90 is described here in terms of a pulley-and-belt drive mechanism, however, any of a number of bi-directional linear drive mechanisms may be employed to achieve the purpose of linearly moving a sample tube rack 42 in either of two opposing directions. FIG. 3B illustrates a plurality of sample tube racks 42 coupled to each drive belt 85 and 93 by means of a plurality of upright posts 112 generally equally spaced apart by a predetermined distance, and, as seen in FIG. 3B, the plurality of upright posts 112 are attached to belts 85 and 93 at that same predetermined distance. Posts 112 are adapted by any of various mechanical techniques, such as screws, snaps, welds, etc., to secure the plurality of magnetic sample tube racks 42 to belt 85 and 93.

After sample has been aspirated by sampling arm 44 described next and deposited within aliquot wells 52W, sample tube racks 42 may optionally be inventoried within analyzer 10 inside an environmental chamber 38 as described in co-pending application Ser. No.: 09/827,045 also assigned to the assignee of the present invention. Patient liquid specimens contained in open sample tubes 40 are identified by reading bar coded indicia placed thereon using a conventional bar code reader to determine, among other items, a patient's identity, the tests to be performed, if a sample aliquot is desired to be retained inside environmental chamber 38 and if so, for what period of time. It is also common practice to place bar coded indicia on sample tube racks 42 and employ a large number of conventional bar code readers installed throughout analyzer 10 in order to ascertain, control and track the location of both sample tubes 40 and sample tube racks 42. Such reader devices and the techniques for tracking are well known in the art and are not seen in FIG. 1 nor need be discussed further.

Figure 4:
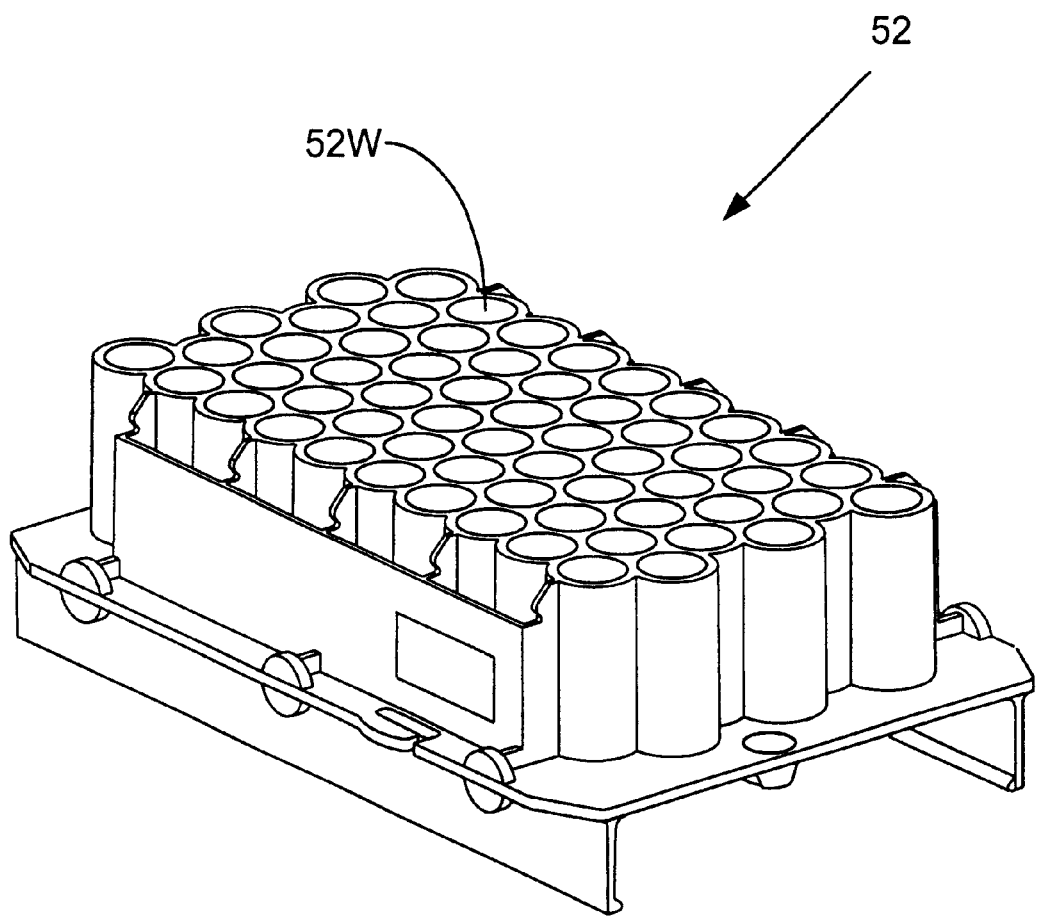
FIG. 4 is a perspective view of a multi-well aliquot vessel useful in practicing the present.

A fluid sampling arm 44 supports a conventional liquid sampling probe 46 and is mounted to a rotatable shaft 48 so that movement of sampling arm 44 describes an arc intersecting the sample tube transport system 36 and an aliquot strip transport system 50 adapted to transport multi-well aliquot vessels 52, like that seen in FIG. 4, to a conventional sample/reagent aspiration and dispense arm 54 located proximate reaction carousel 12. Sampling arm 44 is operable to aspirate liquid sample from sample tubes 40 and to dispense a sample aliquot into one or more of a plurality of aliquot wells 52W in aliquot vessels 52, depending on the quantity of sample required to perform the requisite assays and to provide for a sample aliquot to be retained by analyzer 10 within environmental chamber 38. Another sample aspiration and dispense arm 54 is controlled by computer 15 and is adapted to aspirate a controlled amount of sample from wells 52W via a conventional nozzle 54N and to dispense an appropriate amount of aspirated sample into one or more cuvettes 24 for assay testing for one or more analytes. After sample has been dispensed into reaction cuvettes 24 in cuvette ports 20 and 22, conventional transfer means move aliquot strips 52 as required between aliquot strip transport system 50 and environmental chamber 38 or, optionally, to a waste disposal area, not shown.

Analyzer 10 is controlled by computer 15 based on software written in a machine language, like that used on the Dimension® clinical chemistry analyzer sold by Dade Behring Inc, of Deerfield, Ill., and widely used by those skilled in the art of computer-based electromechanical control programming. At least two reagent aspiration and dispense arms 56 and 58 comprising a pair of conventional liquid reagent probes, 56P and 58P, respectively, are independently mounted and translatable between reagent storage areas 36 and 28, respectively. Probes 56P and 58P are shown in FIG. 1 in two operating positions, with one probe, 56P, adapted to remove reagent from a reagent container in storage area 26 and to dispense aspirated reagent into cuvettes 22 and 24 located in cuvette circles 14 and 16 and with the other probe, 58P, adapted to remove reagent from a reagent container in storage area 28 and to dispense aspirated reagent into cuvettes 22 and 24 located in cuvette circles 14 and 16. Probes 56P and 58P typically comprise an ultrasonic mechanism used for hydrating, aspirating, dispensing and mixing reagents. The hydrating, aspirating, dispensing and mixing mechanisms have features well known in the art and need not be described further.

Cuvette load and unload stations 60 and 62 are positioned proximate outer cuvette carousel 14 and are conventionally adapted to load cuvettes 24 into cuvette ports 20 and 22 seen in FIG. 2 formed in outer cuvette carousel 14 and inner carousel 16 using for example a translatable robotic clamp 64. Conventional sample processing devices 34 (FIG. 2), are positioned at selected circumferential locations about the reaction carousel 12 in order to access reaction cuvettes 26. Processing devices 34 are adapted to provide, among other processing steps, for mixing together of the sample liquid and the reagent liquid contained in cuvettes 24, for washing the sample liquid and the reagent liquid contained in cuvettes 24, and for magnetic separation of tagged magnetic particles from free tags or reagent liquid contained in cuvettes 24.

Various assay analyzing stations 66 may be located proximate outer reaction carousel 12 and are adapted to measure light absorbency in or emission from cuvettes 24 at various wavelengths, from which the presence of analyte in the sample liquid may be determined using well-known analytical techniques. Stations 66 typically comprise conventional photometric, fluorometric or luminescent measuring devices adapted to perform an interrogating measurement at any convenient time interval during which reaction carousel 12 is stationary.

Drive means are provided for independently rotating outer reaction carousel 12 about an axis, the drive means typically comprising gear teeth disposed on the carousel 12 and interlacing with pinion gears mounted on the shaft of a motor. The drive means may be of conventional design and are not illustrated.

Figure 5:
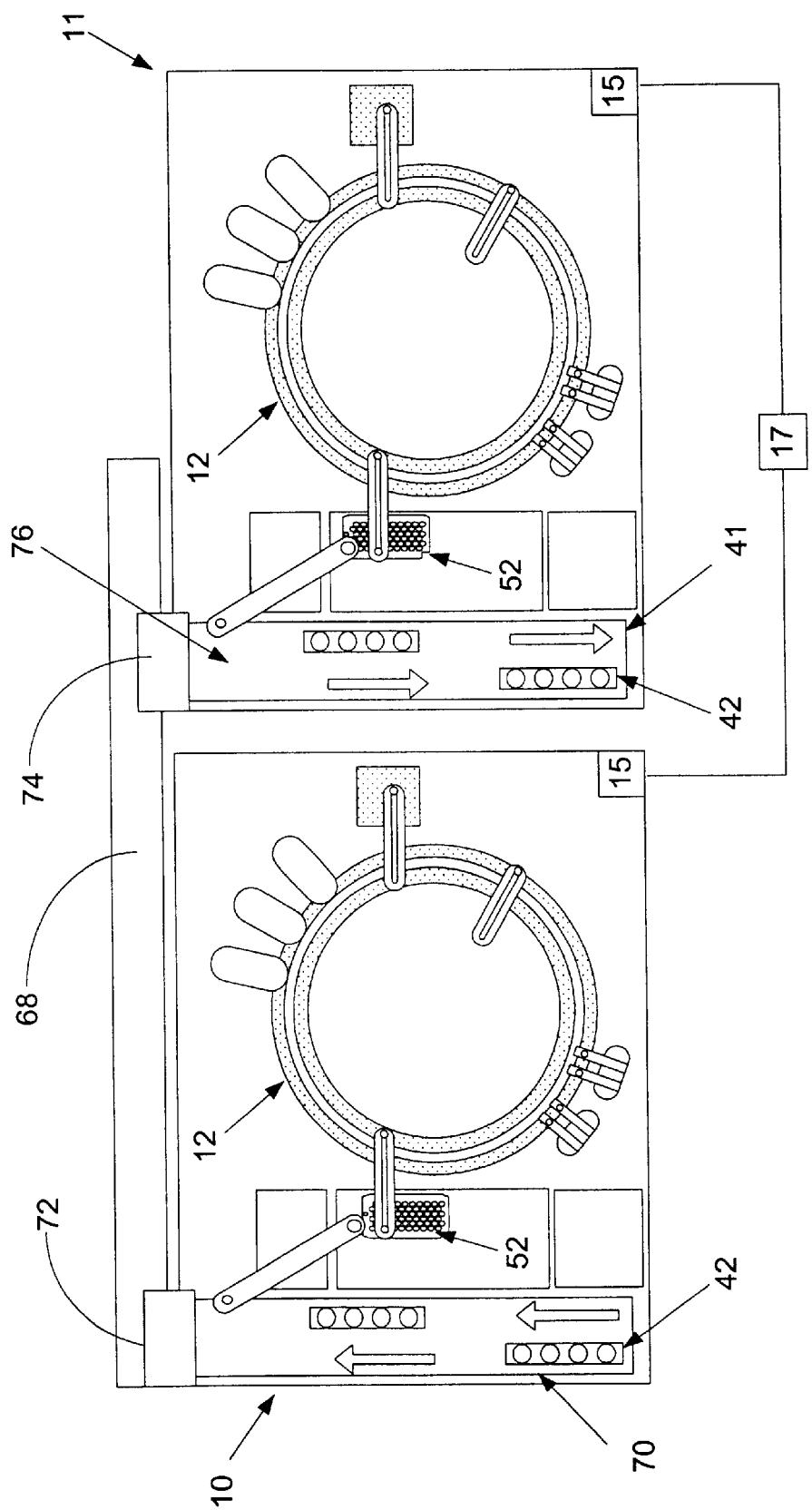
FIG. 5 is a schematic plan view of a pair of automated clinical analyzers like those of FIG. 1, operated as taught by a first embodiment of the present invention.

A principal object of the invention is to provide a method for operating a pair of automatic clinical analyzers 10 and 11 linked together by a bi-directional shuttle 68 as shown in FIG. 5 in a manner that maintains throughput regardless of an operational failure within the system. In this instance, the individual computers 15 of analyzers 10 may be cooperatively controlled by a stand-alone computer 17 so programmed using well known techniques, or a single one of the computers 15 may alternately be programmed so as to control both analyzers 10 and 11.

Analyzers 10 and 11 are essentially identical to one another except that the menu of assays capable of being performed thereon is selectively different as explained previously. For convenience in describing operation of the pair of automatic clinical analyzers 10, the rightmost analyzer is identified as analyzer 11. In the multi-analyzer system seen in FIGS. 5 and 6, when analyzer 10 is attached to bi-directional shuttle 68, an appropriate sensor 10S detects the linking together of the two mechanisms and the bi-directional incoming and outgoing sample rack transport system 36 of analyzer 10 is automatically converted by computer 15 of analyzer 10 into a one-way incoming sample rack transport system 70 adapted to receive all sample tube racks 42 having sample tubes 40 to be analyzer by either analyzer 10 or 11, such conversion being simply accomplished by reversing the direction of movement of a single one of the two bi-directional linear drive transport mechanisms 90LT seen in FIG. 3A. Sensor 10S is preferably of an electronic design and is adapted to interface with bi-directional shuttle 68 so that the presence, or absence of a previously attached analyzer, like analyzer 11, is also detected. The necessity of determining if analyzer 10 is the first, or only analyzer attached to bi-directional shuttle 68, derives from the need to ascertain whether the bi-directional incoming and outgoing sample rack transport system 36 of analyzer 10 is functionally converted into a one-way incoming sample rack transport system 70 or into a one-way outgoing sample rack transport system 76 in the event another analyzer has already been attached to bi-directional shuttle 68. In other words, the two analyzers of FIG. 5 are equipped with sensors 10S and 11S each interacting with bi-directional shuttle 68 so that whenever either analyzer 10 or 11 is initially linked with bi-directional shuttle 68, the analyzer is able to determine whether its sample rack transport system should be automatically converted into a bi-directional incoming or outgoing sample rack transport system, suitable for use in a multi-analyzer system like that seen in FIGS. 5 and 6. Devices like sensors 10S and 11S, as well as the associated electronic controls and control logic are generally of a conventional design and known to clinical analyzer design artisans. In the linking together of both analyzers 10 and 11, then, in the instance that analyzer 10 is the first analyzer linked to bi-directional shuttle 68, sensor 10S determines such a state, and the bi-directional incoming and outgoing sample rack transport system 36 of analyzer 10, seen in FIG. 1, is functionally converted into a one-way incoming sample rack transport system 70, seen in FIG. 6. Subsequently, when analyzer 11 is the second analyzer linked to bi-directional shuttle 68, sensor 11S determines such a state, and the bi-directional incoming and outgoing sample rack transport system 36 of analyzer 10, seen in FIG. 1, is functionally converted into a one-way outgoing sample rack transport system 76, seen in FIG. 6, and analyzer 10 is automatically changed into analyzer 11, with respect to their respective sample rack transport systems. Obviously, an operator may make the above described changes by entering appropriate computer commands into any or all of computers 15 and 17.

Any single sample tube rack 42 may then be transferred from incoming sample rack transport system 70 by a first conventional rack transfer device 72 operable between analyzer 10 and bi-directional shuttle 68 and removed from shuttle 68 via a similar second conventional rack transfer device 74 onto analyzer 11 when directed by computer 17 or by direct operator intervention. In the instance described here when two analyzers 10 and 11 are linked together by shuttle 68, the original bi-directional incoming and outgoing sample rack transport system 36 of analyzer 11 may also be automatically converted into a one-way outgoing transport system 76 adapted to dispose of all sample tube racks 42 having sample tubes 40 with samples finally analyzed by either analyzer 10 or 11. Operation and features of a transport device like shuttle 68 are well known in the art, for example as discussed in U.S. Pat. Nos. 6,117,392 and 6,117,683 and 6,141,602, and are thus not provided here. Generally, conveyor belts, hooks, magnetic devices, or the like may be employed in the design of incoming transport system 70, first transfer mechanism 72, second transfer mechanism 74, and outgoing transport system 76.

One important feature of the present invention is the bi-directional design of shuttle 68 being adapted to move a single sample rack or a similar device at a single time in-between analyzers 10 and 11. In other words, only a single sample rack or only a similar device resides in transit on bi-directional shuttle 68 in-between analyzers 10 and 11. Consequently, shuttle 68 provides for total random-access movement of sample racks 40 between analyzers 10 and 11, without the restrictions on freedom of movement associated with batch-like or sequential load and unload movement of sample racks 40 between analyzers 10 and 11 as experienced by conveyor systems adapted to simultaneously move more than one sample rack as is frequently found in the art. The combination of bi-directional shuttle 68, incoming transport system 70, first transfer mechanism 72, second transfer mechanism 74, and outgoing transport system 76 provide for fully unrestricted random access of any single sample rack 40 within system 10 to either of analyzer 10 or 11.

An additional feature of the present invention is storing a number of "special" reagent cartridges 31", seen in FIG. 2 and removed as required from reagent management system RMS, within reagent storage areas 26 or 28, the special reagent cartridges 31 not containing chemicals generally considered as reagents needed to perform assays, instead containing solutions known in the industry as calibration and control solutions. Calibration of automated clinical is well known for requiring the definition of a mathematical relationship between the concentration of the analyte of interest and the detection signal generated by measuring devices 66. These relationships are generally non linear such that a system requires that calibration tests be made on a small number of multiple standardized solutions to define the signal-analyte relationship. Standardized or calibration solutions are a family of controlled formulation solutions, each of which contains accurately predetermined quantities or concentrations of analytes of interest. Concentrations that are substantially lower and higher than normal are generally employed. After the relationship between test signal values and analyte concentrations on an analyzer has been establish Ted using such standard solutions, other solutions containing known amounts of analyte more representative of a patient's actual analyte levels, known as control solutions, are routinely run as a quality control measure on an analyzer to confirm that all functions and operations on an analyzer remain within normal operating range. In the same manner as sample racks 42 may be moved by shuttle 68, seen in FIG. 6, between analyzers 10 and 11, the present invention also provides cartridge transport devices 84 of a conventional design and operable between analyzers 10 and 11 and bi-directional shuttle 68 so that any reagent cartridge 30 or calibrator or control cartridge 31 may routinely be shuttled on demand by computer 17 from reagent storage areas 26 and 28 of either analyzer 10 or 11, along bi-directional shuttle 68, to either analyzer 10 or 11. Such a feature thus enables random-access movement of sample racks 40 and reagent cartridges 30 and 31 between analyzers 10 and 11, without any restrictions on freedom of movement. The combination of bi-directional shuttle 68, incoming transport system 70, first transfer mechanism 72, second transfer mechanism 74, outgoing transport system 76 and cartridge transport devices 84 provide the ability to singly move any sample rack 42 or any reagent cartridge 30 or 31 to either of analyzer 10 or 11, by only taking consideration for whether or not bi-directional shuttle 68 is already occupied with another single sample rack 42 or any reagent cartridge 30 or 31, providing advantageous flexibility in comparison to multi-analyzer systems like found in the prior art and previously described.

Figure 6:
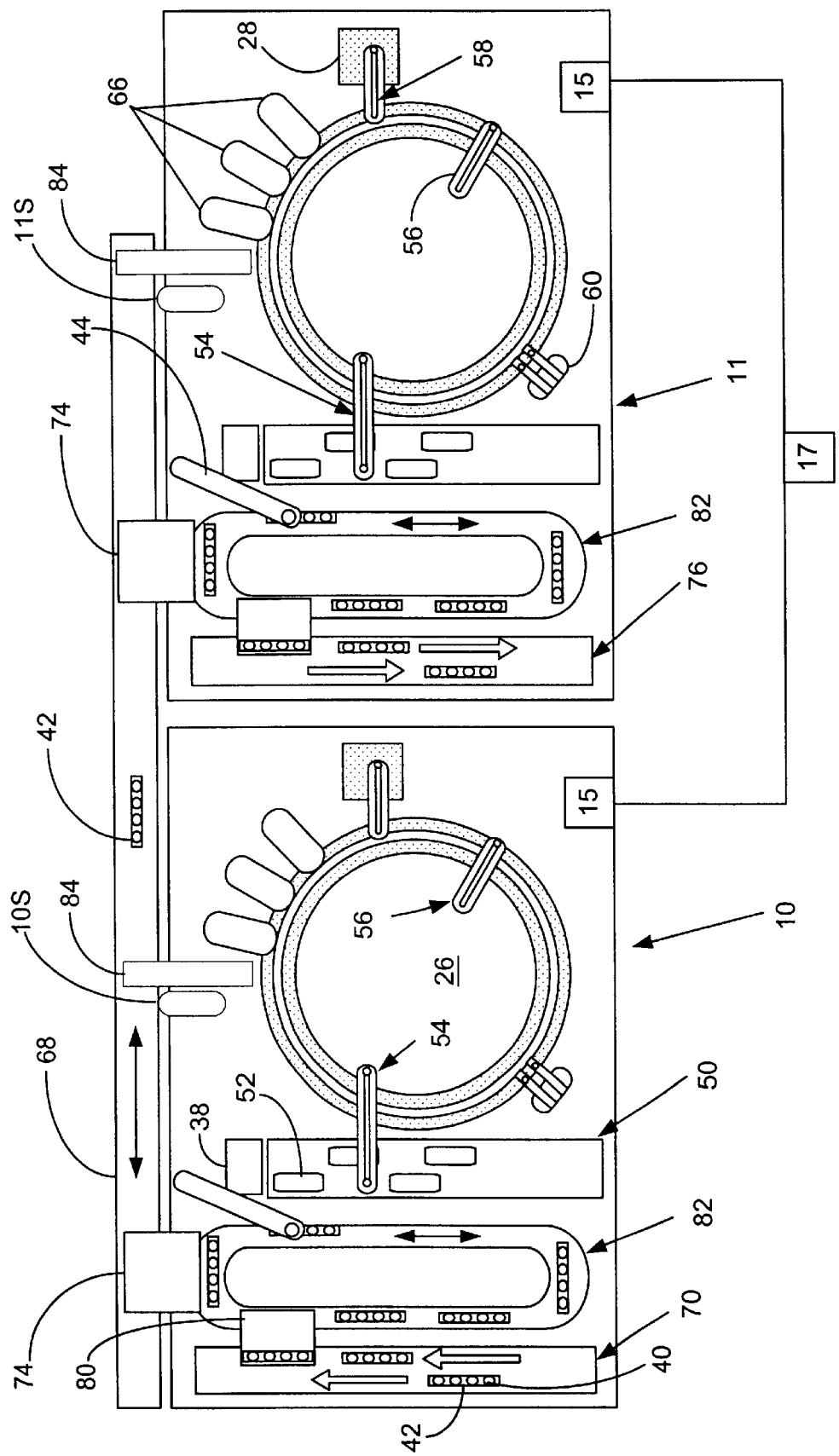
FIG. 6 is a schematic plan view of a pair of automated clinical analyzers like those of FIG. 1, operated as taught by another embodiment of the present invention; and, FIG. 7 is a schematic plan view of an analyzer system having at least two analyzers as taught by the present invention.

The advantages of the present invention become apparent when one of several situations are encountered in active operation of a multi-analyzer system like seen in FIG. 6 within a clinical laboratory. For reasons of overall throughput of assays in a multi-analyzer system, it is conventional to have each analyzer equipped to perform different groupings of system menu assays. The term "system menu assays" is intended to mean the assays either of analyzers 10 and 11 are designed for and capable of being performed including necessary reagents or other specialty items like calibration or control solutions either loaded onto the analyzer or automatically available from reagent management system RMS using reagent management system transport 29. Likewise, the term "analyzer menu assays" is intended to mean the particular assays a single analyzer 10 or 11 is designed for and capable of being performed including necessary reagents or other specialty items already being loaded onto the analyzer. As illustrated in FIG. 6, in the first instance that an operational analyzing portion of either analyzer 10 or 11 experience a software, optical, electromechanical, chemical or other failure, then due to the just described combination of bi-directional shuttle 68, incoming transport system 70, first transfer mechanism 72, second transfer mechanism 74, outgoing transport system 76 and cartridge transport devices 84, the present invention provides the ability to singly move any sample rack 42 or any reagent cartridge 30 or 31 to either of analyzer 10 or 11, so that the analyzer menu assays of a disabled analyzer may be replicated or added upon an operational analyzer. For example, if the measuring stations 66, cuvette load and unload stations 60 and 62, sample processing devices 34, liquid reagent probes, 56P and 58P or the like of analyzer 10 become disabled, then the cartridge transport devices 84 on analyzers 10 and 11, in cooperation with bi-directional shuttle 68, may be operated so that any reagent cartridge 30 or calibrator or control cartridge 31 needed to replicate the analyzer menu assays of analyzer 10 onto analyzer 11 may routinely shuttled on demand by computer 17 from reagent storage areas 26 and 28 from analyzer 10 or reagent management system RMS, along bi-directional shuttle 68, to analyzer 11 and the clinical laboratory is no longer incapable of performing those analyzer menu assays of analyzer 10.

Alternately, in order to achieve high overall throughput of assays in commercially available multi-modular analyzer systems, number of different assay format types are each performed each on a different and dedicated modular analyzer and the modular analyzers are linked by a high-speed mass multi-sample conveyor system. For example, an analyzer may be designed so that a conveyor system transports samples from a sample entrance zone serially past a ion-selective-electrode high volume analyzer, and samples removed from the conveyor, tested for ionic analytes and returned to the conveyor, to a chemistry medium volume analyzer, and samples removed from the conveyor, tested for chemistry analytes and returned to the conveyor, to an immunoassay lower volume analyzer, and samples removed from the conveyor, tested for immunizes and returned to the conveyor, and finally collected at a sample exit zone. Unfortunately, in the event of an operational failure in any of the analytical modules or conveyor system, the full multi-modular system becomes unavailable for assaying samples. As explained above, the present invention provides a significant improvement over such an arrangement in that if any operational portion of either analyzer 10 or 11 experience an operational failure, then due to the described combination of bi-directional shuttle 68, incoming transport system 70, first transfer mechanism 72, second transfer mechanism 74, outgoing transport system 76 and cartridge transport devices 84, the present invention provides the ability to singly move any sample rack 42 or any reagent cartridge 30 or 31 to either of analyzer 10 or 11, so that the analyzer menu assays of a disabled analyzer may be replicated or added upon an operational analyzer.

Similarly, in the second instance that an unusually large number of incoming patient samples are scheduled for analyzer menu assays of analyzer 10 and not those found on analyzer 11, for instance in the event of a major accident or disaster requiring a large volume of special assays, then again, by means of the just described combination of bi-directional shuttle 68, incoming transport system 70, first transfer mechanism 72, second transfer mechanism 74, outgoing transport system 76 and cartridge transport devices 84, the present invention provides the ability to singly move additional reagent cartridges 30 or 31 to analyzer 11, so that the analyzer menu assays of an "overloaded" analyzer 10 may be replicated or added upon analyzer 11, analyzer 11 may be automatically calibrated using the appropriate special reagent cartridges to provide calibration solutions, adding additional assay capability to the multi-analyzer system thereby materially increasing throughput beyond the capabilities of a single analyzer 11.

Even more importantly, if the bi-directional shuttle 68 were disabled, then in the reverse manner in which the two stand-alone analyzers 10 and 11 were initially linked by shuttle 68, then either in response to a command from computer 17 or by direct operator intervention, the one-way incoming sample rack transport system 70 of analyzer 10 can be immediately re-converted back into the bi-directional incoming and outgoing sample rack transport system 36 so that analyzer 10 becomes fully functional and clinical testing may resume. Similarly, the one-way outgoing sample rack transport system 76 of analyzer 11 would be re-converted back into the original bi-directional incoming and outgoing sample rack transport system 36 of analyzer 11. This feature of the present invention provides a major advantage over prior art systems employing a conveyor to move samples to be tested between analyzers or analytical modules since in the event of such a disabled conveyor, the prior art systems become totally disabled until the conveyor is repaired, even though the analyzers or analytical modules may be fully operational.

Similarly, if either of the one-way incoming sample rack transport system 70 of analyzer 10 or the one-way outgoing sample rack transport system 76 of analyzer 11 became disabled or experienced a transport operational or functional failure, then the one-way incoming sample rack transport system 70 of analyzer 10 can be immediately re-converted back into the bi-directional incoming and outgoing sample rack transport system 36 so that analyzer 10 becomes fully functional and clinical testing may resume, or the one-way outgoing sample rack transport system 76 of analyzer 11 would be re-converted back into the original bi-directional incoming and outgoing sample rack transport system 36 of analyzer 11. This feature of the present invention provides an additional major advantage over prior art systems employing a single sample entry zone or single sample exit zone to introduce samples to be tested or remove samples finally tested from either a series of analyzers or analytical modules since in the event of such a disabled single sample entry zone or single sample exit zone, the prior art systems become totally disabled until either the single sample entry zone or single sample exit zone are repaired, even though the analyzers or analytical modules may be fully operational.

Figure 7:
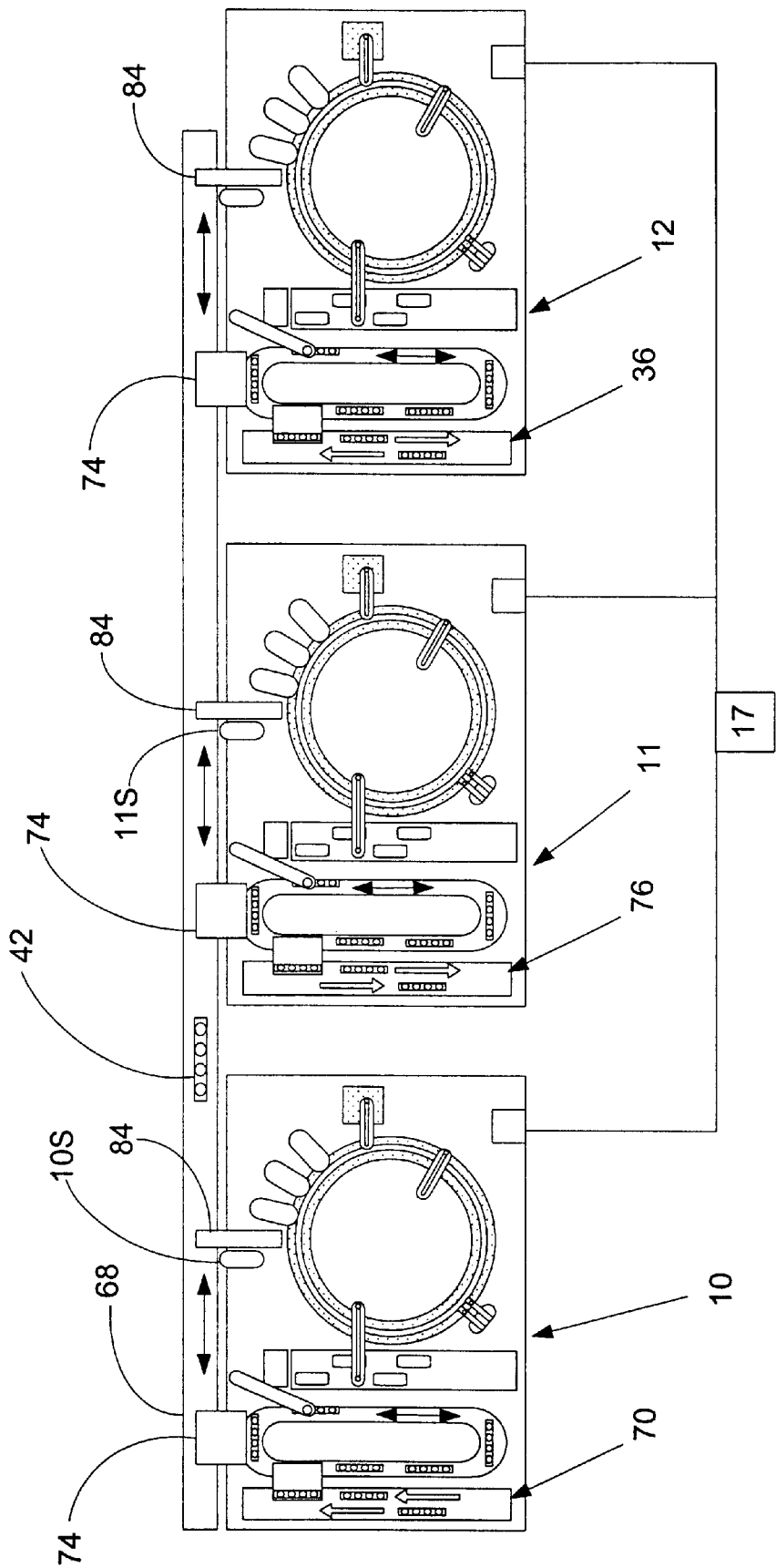

The details of performing a myriad of assays within a multi-analyzer system and controlling the routing of samples or reagents and the like are tasks regularly encountered within the art and need not be described herein. It is sufficient that the teachings of the present invention, wherein at least two automatic clinical analyzers are linked together by a bi-directional shuttle, the bi-directional shuttle adapted to move a sample rack or a similar device between said analyzers. The analyzers are essentially machine-wise identical to one another except that the menu of assays capable of being performed on the individual analyzers may be optionally and selectively different; i. e., all analyzers in the multi-analyzer system are equipped with functionally identical sample handling, reagent storage and sample processing and assaying devices, etc. However, the analyzers may be equipped with a slightly different inventory of reagents stored on-board each so that the analyzers are initially capable of performing a different menu of assays. In a stand-alone mode, each analyzer has an independently operable bi-directional incoming and outgoing automated sample rack transport system, so that samples to be tested may be placed onto an analyzer, automatically subjected to the requested assay protocols, and returned to an inventory of samples finally tested. However, when the machines are linked together by a bi-directional shuttle, the bi-directional incoming and outgoing sample rack transport system of one of the analyzers is automatically converted into a one-way incoming sample rack transport system adapted to receive all sample racks carrying sample tubes to be analyzer by any analyzer. In a similar manner, the incoming sample tube transport system of another of the analyzers is automatically converted into a one-way outgoing transport system adapted to dispose of all sample racks having sample tubes with samples finally tested by an analyzer. Because the bi-directional shuttle is adapted to move only a single sample rack or similar device between analyzers, in the event that one of the analyzers experiences an operating failure or in the event that the bi-directional shuttle experiences an operating failure, the analyzer system may automatically revert to a stand-alone analyzer system employing only the operational analyzer and samples may be supplied only to and analyzed only by the operational analyzer, need only be presented to such artisans so that an previously unachievable increase in analyzer throughput be achieved. FIG. 7 is a schematic plan view of an analyzer system having at least two analyzers, analyzers 10, 11 and 12 as taught by the present invention connected together in a manner that ensures optimum system throughput. In this instance, analyzers 10 and 11 are operated such that analyzer 10 employs a one-way incoming sample rack transport system 70, analyzer 11 employs a one-way outgoing sample rack transport system 76, like seen in FIGS. 5 and 6, and analyzer 12 employs a bi-directional incoming and outgoing automated sample rack transport system 36 like seen in FIG. 1. Such an operational state would be selected by computer 17 in the event of a very high volume of routine-timing patient samples, computer 17 controlling analyzers 10 and 11, bi-directional shuttle 68, incoming transport system 70, first transfer mechanism 72, second transfer mechanism 74, outgoing transport system 76 and cartridge transport devices 84, so that the analyzer menu assays of an "overloaded" analyzer 10 may be replicated or added upon analyzer 11. At the same time, analyzer 12 may be operated with bi-directional incoming and outgoing automated sample rack transport system 36 enabling, for instance, a small number of high priority patent samples to be processed at the same time that the volume of routine-timing patient samples are conducted on analyzers 10 and 11. Clearly a variety of operational modes may be chosen to optimize throughput of a linked multi-analyzer system as taught by the present invention by using any combination of incoming transport system 70, outgoing transport system 76 and bi-directional incoming and outgoing automated sample rack transport system 36.

It is to be understood that the embodiments of the invention disclosed herein are illustrative of the principles of the invention and that other modifications may be employed which are still within the scope of the invention. Thus the present invention is not limited to those embodiments precisely shown and described in the specification but only by the claims.

What is claimed is:

1. A computer controlled automated clinical analyzer system having at least two stand-alone automatic clinical analyzers, each analyzer having a bi-directional incoming and outgoing sample transport system, the system further comprising a bi-directional shuttle linking together the analyzers, and control means for controlling the system being controlled such that the bi-directional incoming and outgoing sample transport system of a first analyzer is automatically converted into a one-way incoming sample transport system adapted to receive all samples to be analyzed by said system, and the bi-directional incoming and outgoing of a second analyzer is automatically converted into a one-way outgoing transport system adapted to dispose of all samples analyzed by either analyzer.

2. The automated clinical analyzer system of claim 1 wherein the system is controlled such that if any one of the analyzers experiences an analytical operating failure, the analyzer system automatically reverts to a stand-alone analyzer system in which samples are supplied only to and analyzed only by an fully functional analyzer.

3. The automated clinical analyzer system of claim 1 wherein the system is controlled such that if the bi-directional shuttle experiences an operating failure, the analyzer system automatically reverts to a stand-alone analyzer system in which samples are supplied only to and analyzed only by a stand-alone analyzer.

4. The automated clinical analyzer system of claim 1 wherein the system is further controlled such that if the one-way incoming sample transport system of the first analyzer experiences a functional failure, then the one-way outgoing transport system of the second analyzer is automatically re-converted into a bi-directional incoming and outgoing sample rack transport system.

5. The automated clinical analyzer system of claim 1 wherein the system is further controlled such that if the one-way outgoing sample transport system of the second analyzer experiences a functional failure, then the one-way incoming transport system of the first analyzer is automatically re-converted into a bi-directional incoming and outgoing sample rack transport system.

6. The automated clinical analyzer system of claim 1 wherein the analyzers have different analyzer menu assays, each analyzer further comprising a reagent cartridge transporter adapted to transport reagent, calibrator and control cartridges and wherein the system is controlled such that if any one of the analyzers experiences an analyzing operational failure, the reagent cartridge transporter and the bi-directional shuttle are controlled to replicate the analyzer menu assays of the analyzer experiencing an analyzing operating failure upon a operational analyzer.

7. The automated clinical analyzer system of claim 1 wherein if an unusually large number of patient samples are scheduled for a particular assay in the analyzer menu assay of a first analyzer and said particular assay is not within the analyzer menu assay of a second analyzer, then the reagent cartridge transporter of the first analyzer and the bi-directional shuttle are controlled to add the particular assay in the analyzer menu assay of the first analyzer within the analyzer menu of the second analyzer.

* * * * *